US008888362B2

(12) United States Patent
Hart et al.

(10) Patent No.: US 8,888,362 B2
(45) Date of Patent: Nov. 18, 2014

(54) THERMAL PHASE SEPARATION SIMULATOR (75) Inventors: Paul R. Hart, Sugar Land, TX (US); Lee E. Nuebling, The Woodlands, TX (US); Robert R. Cleary, Pearland, TX (US); Virgil T. Little, Missouri City, TX (US); Jan H. Beetge, Pearland, TX (US)

(73) Assignee: Ecolab USA Inc., St. Paul, MN (US)

( * ) Notice: Subject to any disclaimer, the term of this patent is extended or adjusted under 35 U.S.C. 154(b) by 146 days.

(21) Appl. No.: 13/399,663

(22) Filed: Feb. 17, 2012

(65) Prior Publication Data
US 2012/0212729 A1 Aug. 23, 2012

Related U.S. Application Data (60) Provisional application No. 61/443,865, filed on Feb. 17, 2011.

(51) Int. Cl.
*G01N 25/00* (2006.01)
*G01K 1/00* (2006.01)
(Continued)

(52) U.S. Cl.
CPC .......... *B01D 17/041* (2013.01); *B01D 17/0217* (2013.01); *B01J 2219/00011* (2013.01); *B01L 2300/0627* (2013.01); *G01N 2021/5976* (2013.01); *B01L 7/00* (2013.01); *B01D 17/042* (2013.01); *B01L 2300/0803* (2013.01); *B01L 2300/1827* (2013.01); *B01L 3/50825* (2013.01); *B01L 9/06* (2013.01); *C40B 60/12* (2013.01); *B01F 11/0008* (2013.01); *B01L 2200/147* (2013.01)
USPC ................ 374/45; 374/208; 436/43

(58) Field of Classification Search
USPC ......... 374/45, 46; 356/51; 422/64, 63, 50, 62, 422/81
See application file for complete search history.

(56) References Cited

U.S. PATENT DOCUMENTS 5,863,752 A * 1/1999 Court et al. ...................... 435/34
6,245,289 B1 * 6/2001 Dodd .............................. 420/60
(Continued)

FOREIGN PATENT DOCUMENTS

WO WO2011/156084 A1 12/2011

OTHER PUBLICATIONS

Champion Technologies PCT/US20012/025662 "International Preliminary Report on Patentabililty", PCT Adavance E-Mail; Aug. 29, 2013, 7 pages. (This PCT application is related to the present U.S. Appl. No. 13/399,663).

(Continued)

*Primary Examiner* — Lisa Caputo
*Assistant Examiner* — Nasir U Ahmed
(74) *Attorney, Agent, or Firm* — Senniger Powers LLP (57) ABSTRACT A thermal phase separation simulator and method for testing chemicals is disclosed. The simulator comprises a circular block heater carousel mounted for rotation on a stage. The carousel includes a circular array of test wells for receiving a plurality of test bottles, a plurality of heating elements and thermocouples disposed between the wells. Each well has an illumination port and a vertical slit to the outside to allow visual observation or imaging of a vertical swatch of the bottle. An illumination source aligns with the illumination port of each well in response to rotation of the carousel. The method includes adding a mixed phase fluid to a plurality of bottles, adding a chemical agent to each bottle, and simulating a thermal phase separation. Images of the fluid in each bottle are captured and analyzed to determine the performance of the one or more chemical agents.

19 Claims, 6 Drawing Sheets (51) Int. Cl.
  B01D 17/02 (2006.01)
  B01L 7/00 (2006.01)
  B01D 17/04 (2006.01)
  C40B 60/12 (2006.01)
  B01F 11/00 (2006.01)
  C12P 37/00 (2006.01)
  G01N 21/59 (2006.01)
  B01L 3/00 (2006.01)
  B01L 9/06 (2006.01)

(56) References Cited

U.S. PATENT DOCUMENTS

| | | | |
|---|---|---|---|
| 6,558,947 B1 * | 5/2003 | Lund et al. | 435/303.1 |
| 6,900,059 B1 * | 5/2005 | Shinn et al. | 436/43 |
| 7,604,985 B2 * | 10/2009 | Bachur et al. | 435/288.7 |
| 2001/0030906 A1 * | 10/2001 | Friedman | 366/114 |
| 2002/0130100 A1 * | 9/2002 | Smith | 215/247 |
| 2005/0276727 A1 * | 12/2005 | Pawliszyn et al. | 422/99 |
| 2008/0247914 A1 * | 10/2008 | Edens et al. | 422/100 |
| 2010/0015720 A1 | 1/2010 | McDaniel et al. | |

OTHER PUBLICATIONS

Duke, "Water Content Test for EOR Crude Simulates Desalter", Marathon Oil Co, Littleton, Colo, 492 Oil & Gas Journal, 89 Feb. 25, 1991 No. 8, Okla., US, XP000206737, 3 pages (40-42).

Dalmazzone, et al. "Development of New "green" Demulsifiers for Oil Production" Institut Francais du Petrole IFP, SPE 65041, Society of Petroleum Engineers Inc., 2001 SPE International Symposium on Oilfield Chemistry held in Houston, Texas, Feb. 13-16, 2001, 9 pages.

Champion Technologies PCT/US20012/025662 "International Search Report and Written Opinion", PCT Adavance E-Mail; Aug. 30, 2012, 13 pages. (This PCT application is related to the present U.S. Appl. No. 13/399,663).

* cited by examiner

THERMAL PHASE SEPARATION SIMULATOR

BACKGROUND OF THE INVENTION

1. Field of Invention

The present invention relates generally to the small-scale simulation of oil-water separators, such as free water knock-outs, heater treaters, and desalters, which are used in the production or processing of petroleum oil. More particularly, the present invention relates to methods for testing so-called thermal production.

2. Background and Related Art

Produced hydrocarbon fluids, such as crude oil and bitumen, naturally contain a variety of immiscible contaminants, such as water, salts, and solids, which have detrimental effects on transport lines and process equipment. The types and amounts of these contaminants vary depending on the particular hydrocarbon fluid. Additionally, water produced with the liquid hydrocarbon fluid, whether native, added, or condensed from steam added to the reservoir, also naturally contains a variety of immiscible contaminants, such as oil, organic solids and inorganic solids, which have detrimental effects on productive use or discharge of the water. The types and amounts of these contaminants vary depending on the particular produced water. Natural or synthetic emulsion stabilizers, such as asphaltenes, naphthenic acid salts, petroleum resins, bi-wet solids, drilling fluids, and the like, can keep the oil and water phases emulsified with each other.

Demulsifying, separating, and purifying these phases are necessary steps before further processing. These processes involve a variety of agitations and stratifications by fluid density for various lengths of time. A variety of diluents, wash fluids, and/or chemicals agents can be added to either or both phases in order to accelerate the process or improve the quality of the processed fluids. High voltage electric fields can be applied to the oil phase to accelerate and improve dehydration. Secondary filtration can be applied to the water phase to accelerate and improve clarification. Concentrated emulsion can be withdrawn from the stratified mesophase or "rag layer" between the two phases in a separator and centrifuged to accelerate and improve the separation. In all these processes, heat is generally added to raise the temperature of the fluids and reduce the viscosity of the fluids. For heavy crudes, oils and bitumens, the temperature is often raised above the boiling point of the water or of the light ends in a diluent added to the oil. This requires elevated pressures to keep the fluids liquid.

Chemical agents that may be added to accelerate and improve removal of water and solids from the hydrocarbon phase are generally known as demulsifiers, emulsion breakers, obverse emulsion breakers, dehydrators, water droppers, solids wetters, or dehazers (for clear fuels). These chemical agents can be added to the oil or to the water that is in contact with the oil. Chemical agents that may be added to accelerate and improve removal of oil and solids from the water phase are generally known as water clarifiers, reverse breakers, reverse emulsion breakers, deoilers, flocculants, coagulants, oil coalescers, or solids wetters. These chemical agents may be added to the water or, in some cases, to the oil that is in contact with the water. Chemical agents that are used to resolve a rag emulsion are often called sluggers, slop treaters, or interface clarifiers. Chemical agents that are used to prevent deposition of solids on surfaces are generally known as dispersants, deposit inhibiters, or antifoulants.

New chemical agents are typically selected and developed using a simple apparatus, such as a set of glass bottles or tubes, and a process referred to as "bottle testing". In the simplest embodiment, emulsion samples and chemical agents are added to the bottles and shaken. The temperature is limited to about 90° C. at atmospheric pressure to keep the water from boiling. The rate of oil-water separation is monitored as a function of time by observing the amount of "free" water that collects at the bottom of the bottle and/or the amount of "free" oil that collects at the top of the bottle, the apparent purity of those phases—the "brightness" of the oil and the "clarity" of the water—and the amount, phase continuity, and coarseness of the emulsion in between the free water and the free oil. Because of the large number of possible chemical agents and combinations of these chemical agents that must be tested to find an appropriate treatment solution, and the unstable nature of the fresh emulsion samples used, the bottle testing needs to be carried out on many samples at once.

The foregoing bottle testing method has proven useful, but does not adequately simulate what happens at the higher temperatures and pressures used to process heavy crudes and bitumens. It has been shown that the surface active agents used for phase separation, as well as those native to the produced oil and water, behave differently at different temperatures.

The process of steam enhanced oil recovery or steam assisted gravity drainage (SAGD) of bitumen is particularly difficult and important to simulate. In an SAGD process, steam is injected into an underground reservoir at temperatures up to 260° C. The steam heats the oil as it condenses to high temperature water and carries the oil or bitumen out of the reservoir as an emulsion at temperatures up to 160° C. under pressures from 100 to 300 psig. A pressure of at least 75 psig is needed to keep water liquid at 160° C. The oil and water mix in highly turbulent flow at this temperature for several minutes to a few hours, then, after cooling to about 130° C., are separated in a series of vessels in which hydrocarbon diluent is added and water is removed. A variety of chemical separation aids are added at various places along oil/gas field production lines and ahead of equipment and vessels.

More sophisticated testing methods using stirred pressure vessels have been used to simulate the temperature and pressure of the separation process, but standard metal vessels do not allow critical visual observations to be made as the fluids separate. Glass, hot oil jacketed, pressure vessels can be used, but these are bulky and expensive to acquire, set up, and control—not amenable to testing many treatments at once in an oilfield environment.

Moreover, test results are highly dependent on the surface properties of small scale test vessels, due to the disproportionate amount of surface area to fluid volume. For example, water can bead-up on the glass around the oil phase instead of sheeting down into the water phase, making it impossible to measure. And the cationic polymers commonly used to separate oil from water irreversibly adsorb onto the anionic glass surfaces, changing the surface wetting for the next test. These polymers must be burned off, chemically or physically, or a layer of glass etched away. This can be difficult and dangerous to do on jacketed glass vessels, especially in the field, and can damage the integrity of the vessel at pressure.

BRIEF SUMMARY OF THE INVENTION

One embodiment of the present invention provides a thermal phase separation simulator for testing chemicals. The simulator comprises a circular block heater carousel made of thermally conductive material and mounted for rotation on a stage. The carousel includes a circular array of test wells for receiving a plurality of test bottles, a plurality of heating elements disposed between the wells for heating the thermally conductive material, and a plurality of thermocouples disposed between the wells for monitoring the temperature of the thermally conductive material. Each well has an illumination port and a vertical slit to the outside to allow visual observation or imaging of a vertical swatch of the bottle. An illumination source aligns with the illumination port of each well in response to rotation of the carousel.

Another embodiment of the present invention provides a method of using the thermal phase separation simulator. The method includes adding a mixed phase fluid to a plurality of bottles, adding one or more chemical agents to each of the bottles, and simulating conditions of a thermal phase separation. Images of the mixed phase fluid in each bottle are captured and analyzed to determine the performance of the one or more chemical agents in aiding separation of the mixed phase fluid.

BRIEF DESCRIPTION OF THE SEVERAL VIEWS OF THE DRAWINGS

Corresponding reference numbers indicate corresponding parts throughout the views of the drawings.

DETAILED DESCRIPTION OF THE INVENTION

This invention is directed to a small-scale batch simulator of oil-water separation processes providing the ability to test a multitude of chemical agents simultaneously using freshly produced emulsion, real process temperatures, agitations, durations, fluid additions and withdrawals. Multiple testing bottles, preferably identical, allow a specific emulsion composition to be analyzed simultaneously, using several different chemical agents, concentrations, and/or addition points, to see which combination provides the most effective treatment.

The simulator includes a bench top carousel capable of rotation about a vertical axis, comprising a circular block heater made of thermally conductive material featuring a circular array of test wells for a multitude of bottles. Each well has an opening in the bottom and a vertical slit to the inside of the block for illumination and a vertical slit to the outside to allow visual observation of a vertical swatch or portion of each test bottle.

The test bottles rest in the wells on rubber o-rings and are held in place with leveraged rubber-tipped latches mounted on the top of the carousel. Unused, disposable glass bottles with burst pressure in excess of 240 psig are used for each test.

The cap in each bottle assembly includes a pressure relief valve with a cracking pressure of 105 psig and a burst pressure of 120 psig. The cap has a compression-sealed, movable dip tube or a compressed rubber septum port that allows, for example, chemicals and diluents to be added and water and oil to be withdrawn. In one embodiment, an electric field is applied to the oil phase by connecting the dip tube to a high voltage source and grounding the heat block.

Heating elements are inserted in the block between every other well to assure symmetrically equivalent heating of the wells. To control and monitor the temperature, two thermocouples are connected: one thermocouple that is mounted next to a heat cartridge feeds a temperature controller, and another thermocouple that is immersed in the fluid inside a bottle verifies the actual test temperature.

The carousel is mounted on an elevated, thermally insulating, slippery-surfaced stage, on a vertical axis such that each bottle can be smoothly rotated in turn past one or more illumination sources placed behind or below the bottle. The carousel has one or more thermally isolated lifting handles with which to turn the carousel, as well as to remove the carousel and mount the carousel sideways on a reciprocal shaker, still connected to power to maintain heat. The shaker has adjustable throw and/or frequency sufficient to replicate agitation in the process simulated.

The carousel and stage are mounted to a bracket that allows for tilting both the carousel and stage sideways in order to shake the bottles in a horizontal position. This bracket allows the carousel to be held in an upright or viewing position or a horizontal shaking position. The carousel may be locked into either position by a locking pin. This bracket can have a hinge and be mounted on a reciprocal shaking table or can stand alone and be lifted and secured onto a separate shaking table.

In another embodiment, mixing of the fluid is done with a physically or magnetically coupled mixer, at a mixing station mounted at a fixed position in the stage. The bottles are mixed in sequence as the carousel is rotated past the mixer. The bottles then rotate past the observation point a fixed time after they were mixed. In another embodiment, magnetic stirrers are placed under all the bottles and the bottles are stirred while the fluids separate and images of the fluid are recorded.

In one embodiment, an imaging device is used to capture images of the fluids, which record the separation of the oil and water in the mixing tubes. The data is processed through an algorithm that computes the volume and the quality of the phases in the bottle.

A thermal phase separation simulator (sometimes referred to herein as the "simulator") provides the ability to test a plurality of chemical agents at the same time. For example, the simulator may use a freshly produced emulsion, and run the test under realistic conditions (i.e., conditions similar to actual field use), such as process temperatures, agitations, durations, fluid additions, fluid withdrawals, and combinations thereof. The simulator uses small amounts of process fluid to perform the experiments, thereby reducing the cost of sample transport and disposal. In the simulator, one or more selected chemical agents, such as chemical demulsifiers, clarifiers, or antifoulants, are added to an oil or water emulsion, and these are mixed together under conditions approximating that of their transport through lines and process equipment. These conditions may include, for example, temperature, amount of shear, duration of mixing, and combinations thereof in order to simulate actual field conditions. Then the oil and water fractions of the emulsions are allowed to separate under conditions approximating that of the separation vessels in the field. These separation conditions may include, for example, temperature, any optional electric field strength that may be applied, residence time, and combinations thereof.

The invention will now be described in detail with reference to the drawings, using preferred embodiments to enable practice of the invention. Although the invention is described with reference to these specific preferred embodiments, it will be understood that the invention is not limited to these preferred embodiments. To the contrary, the invention includes numerous alternatives, modifications, and equivalents as will become apparent to those having ordinary skill in the art from consideration of the following detailed description.

Figure 1:
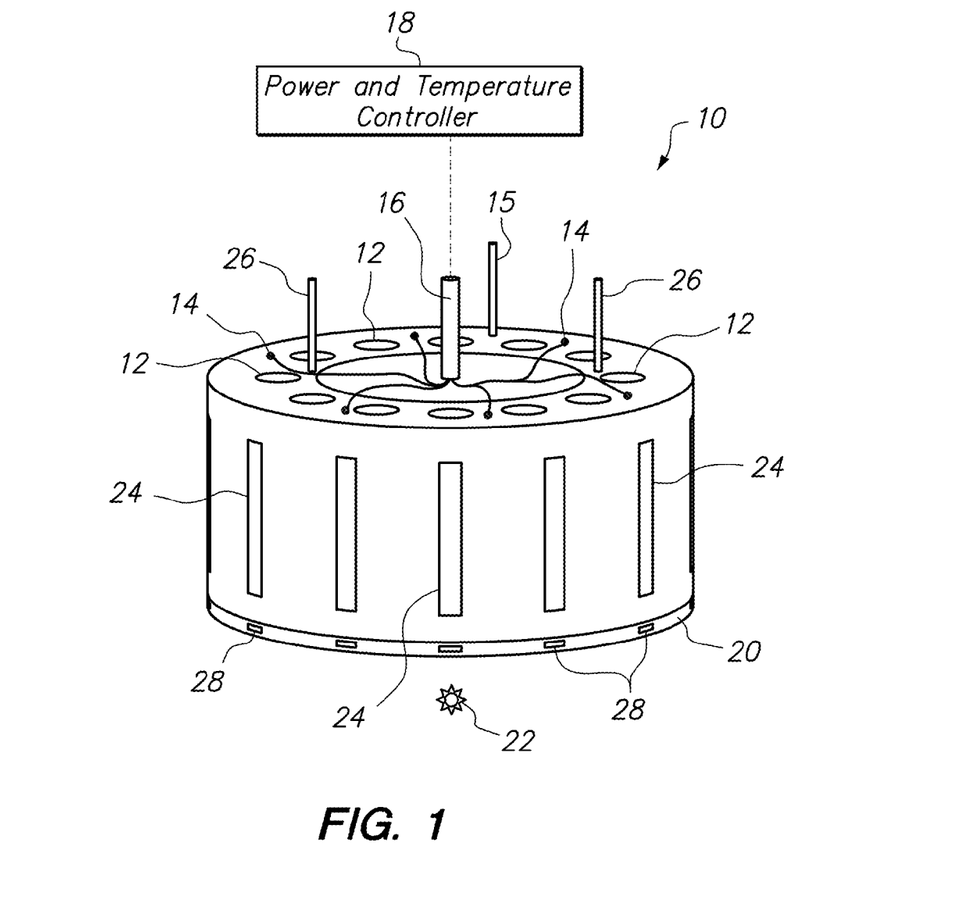
FIG. 1 is a perspective view of a carousel heating block of a simulator.

FIG. 1 is a perspective view of a carousel 10 of a thermal phase simulator. The carousel 10 has a plurality of wells 12 positioned therein and configured to receive up to an equal plurality of testing bottles (see FIG. 6). In the illustrated embodiment, the carousel 10 has twelve cylindrical wells 12 equally spaced along the circumference. Cartridge heating elements 14 (six shown) are inserted into the carousel 10 between every second well 12. There is preferably at least one thermocouple 15 for measuring the temperature of the block between wells where there is no heating element 14. This temperature indicates the extent to which the entire block has been heated. Another thermocouple is preferably associated with at least one of the test bottles, as described in reference to FIG. 4A, below. Both the heating elements 14 and the thermocouples 15 have wiring that extends through a wiring conduit 16 to a power and temperature controller 18. The controller 18 controls the temperature of the carousel 10 and permits the wells 12, along with the bottles and emulsion samples therein, to be heated to a temperature which will best simulate conditions in the field. The appropriate temperature of the fluids in the testing bottles will normally be in the range from about 100° C. to 160° C., so that the water in the testing bottles will not generate pressures over 100 psig.

FIG. 1 also shows the carousel 10 mounted on an elevated, thermally insulating, slippery-surfaced stage 20 on a vertical axis such that the carousel 10 can be rotated and the bottle in each well 12 can be smoothly rotated in turn past fixed mixing or observation points. The stage 20 is connected to a light source 22 such that the light can be directed behind and/or below the bottle observation point. For example, gooseneck fiber optic illuminators may be used. However, one skilled in the art will understand that other illumination angles and methods may be used. In particular, the light source 22 may produce light in the terahertz, infrared, near infrared, visible, ultraviolet, and/or X-ray spectrum and can be of any design known to those skilled in the art. Thus, the slit 24 in the bottle well 12 allows observation of the phase separation process using not only the visible light spectrum, but also other portions of the electromagnetic spectrum that might be advantageous for imaging the fluids. Each slit 24 permits observation of the effects that changing chemical agents, production fluids, diluents, addition points, and other operating conditions have on the phase separation. Optional underside illumination ports 28 may be provided for illumination from the below the wells 12. The carousel 10 also has one or more thermally isolated lifting handles 26 with which to turn the carousel on the stage or remove the carousel from the stage.

Figure 2:
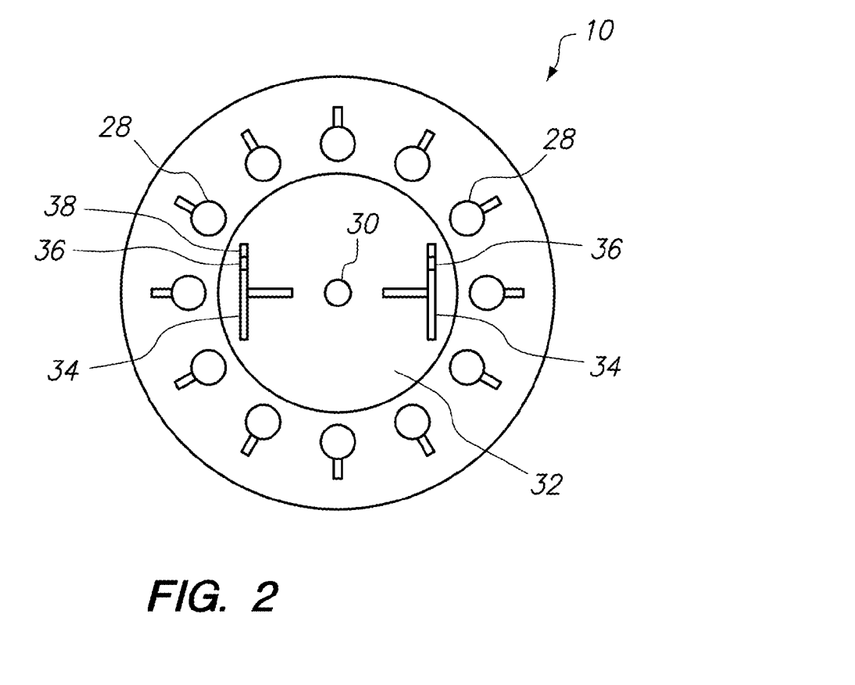
FIG. 2 is a bottom view of the carousel heating block of FIG. 1.

FIG. 2 is a bottom view of the carousel heating block 10 of FIG. 1. The underside illumination ports 28 are shown positioned below each well in the carousel. A pivot shaft 30 is provided in the axial center of the carousel 10 to keep the carousel on the stage during rotation. A mounting plate 32 is secured to the bottom of the carousel 10 to provide a mechanical connection to a tilt mechanism. For example, the tilt mechanism may include a pair of brackets 34 secured to the mounting plate 32, including hinge points 36 and a hole 38 for a locking pin.

Figure 3:
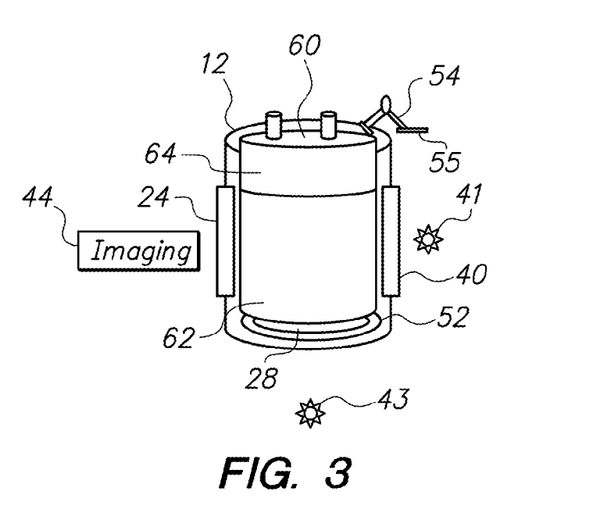
FIG. 3 is a cross sectional close up view of a bottle well in the carousel of FIG. 1.

FIG. 3 is a schematic view of a bottle well 12 in the carousel of FIG. 1. The bottle well 12 includes an exterior viewing window 24, an interior illumination port 40, and an underside illumination port 28. A test bottle 60 rests in the well 12 on a rubber O-ring 52 and is held in place with a rubber-tipped leveraged latch 54 mounted on a top surface 55 of the carousel. A preferred rubber composition is silicone. The carousel heater block (i.e., the well 12) and the latch 54 may also function as secondary containment devices in the unlikely event that the bottle 50 ruptures.

The carousel may be rotated so that the interior illumination port 40 is aligned with an interior optic light source 41 and/or the underside illumination port 28 is aligned with an underside optic light source 43. With the carousel in this position, the condition of the phases within a particular bottle 60 may be easily visually observed. However, the simulator preferably includes an imaging device 44 that is aligned with the one or more light source 41, 43. The imaging device 44 may capture an image of the phases at a particular point in time during a test. By capturing such images at various times during the duration of a test, it is possible to monitor and analyze how one or more variables affect the phases. By capturing similar images for each of the bottles, it is possible to monitor, analyze and compare the performance of one or more chemical agents, one or more concentrations, and the like.

Figure 4A:
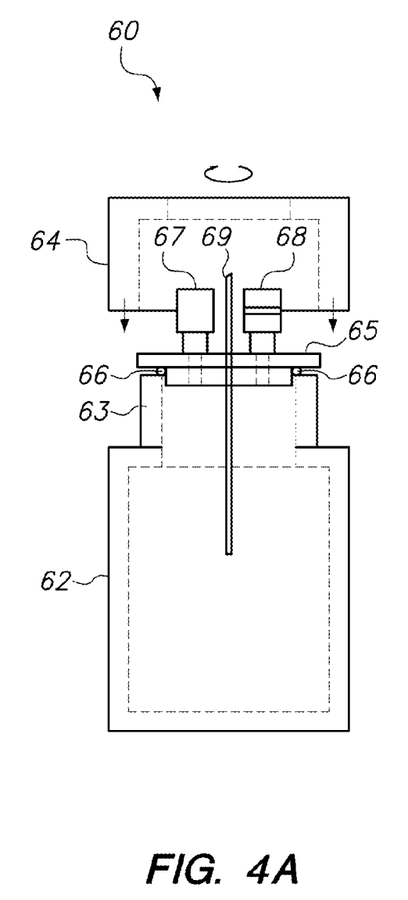
FIG. 4A is a schematic side view of a bottle with a cap having a pressure relief valve and a septum port.

FIG. 4A is a schematic side view of a bottle 60 with a lid 64 having a pressure relief valve 67 and a septum port 68. The lid 64 may be threadably coupled to the bottle body 62 to seal a bottle cap 65 to the bottle lip 63 with an O-ring 66 there between. The cap 65 is fitted with a pressure relief valve 67 with a cracking pressure of 105 psig and a burst pressure of 120 psig (half the burst strength of the bottle). This 105 psig pressure limit allows water temperatures up to 172° C. to be used without boiling. The cap 65 also has a septum port 68. The cap 65 of at least one of the bottles 60 is also fitted with a thermocouple probe 69 to measure the temperature of the fluid in the bottle. The cap 65 may have a separate opening dedicated to the thermocouple probe, or the thermocouple probe may extend through the septum port 68.

Figure 4B:
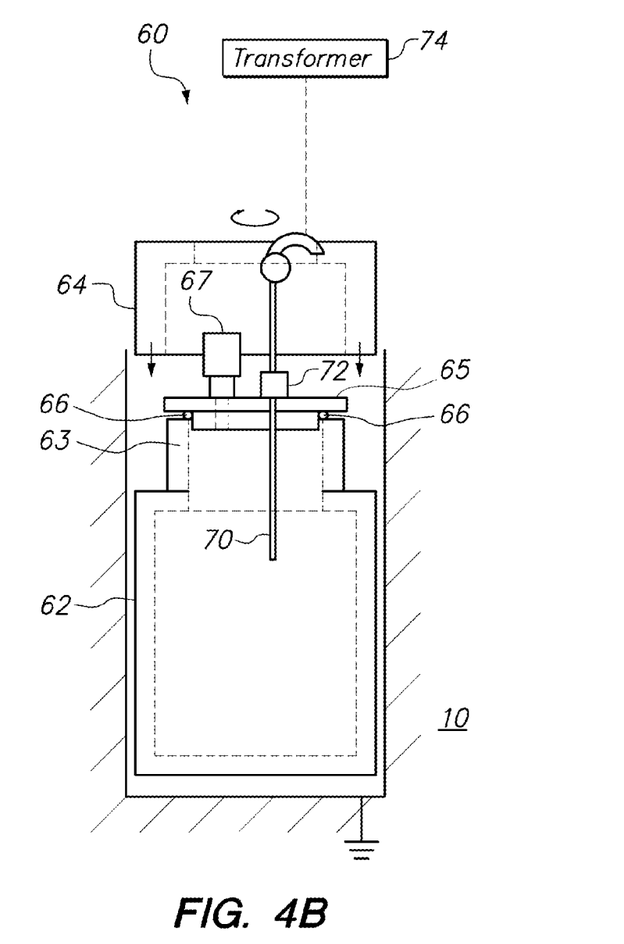
FIG. 4B is a schematic side view of a bottle with a cap having a pressure relief valve and a sealed dip tube.

FIG. 4B is a schematic side view of the bottle 60 with a cap 65 having a pressure relief valve 67 and a sealed dip tube 70. The dip tube 70 may be sealed with a compression seal 72. Other aspects of the bottle 60 and cap 65 are the same as in FIG. 4A.

The movable dip tube 70 can be raised or lowered to any desired position in the bottle. This allows chemicals and diluents to be added to the appropriate phase and allows either water, oil or mesophase emulsion to be selectively withdrawn in the manner of the process being simulated. A spring keeper is used to retain the dip tube should its compression fitting become loose. In one embodiment, the dip tube 70 is electrically isolated by using non-conductive fittings and insulating the exterior exposed metal. Polytetrafluoroethylene (PTFE) or polyetheretherketone (PEEK) are good materials for this insulation as well as for the threaded portion of the cap. The dip tube can then be connected to the high voltage lead of a transformer 74. Electrically grounding the carousel 10 will then impose a radial electric field across the oil layer. To better focus this field, the length of the dip tube can be adjusted to the thickness of the oil layer. A voltage of 5 to 10 kV at 60 Hz is sufficient to oscillate the water droplets in the oil to destabilize the emulsion in the manner of full scale electric field assisted coalescers. Frequencies other than 60 Hz can also be used in the manner of some commercial coalescers. A suitable transformer available commercially is the 10 kV, 23 mA, A10-LA2 model from Dongan. Suitably insulated high voltage leads and plug-in connectors for directing the voltage to the dip tube 70 are also available commercially.

A testing bottle 60, especially the bottle body 62, may be made of glass or other substantially transparent material, such as quartz, diamond, sapphire or clear, thermally stable plastic. Transparent material is used to permit the operator to visually or photographically monitor the phase separation of the samples to obtain experiment results. It is also desirable for the bottle material to be electrically resistive to prevent any significant electrical conduction in the event an electric field is applied across the oil phase. If a multilayer plastic is used, the inside surface should be water wet to allow sheeting of droplets to the bottom.

The bottle walls are thick enough not to break under normal usage in the thermal phase separation simulator. Pressurization to about 100 psig is needed to test water temperatures up to 170° C. without boiling. To provide a good margin for safety, the bottles may have a burst strength of at least 200 psig. A wall thickness of at least two millimeters of borosilicate glass is typically sufficient. The volume of the bottles can vary but the size and shape must match up with the bottle wells in the carousel 10. About 100 mL is generally sufficient.

To assure bottle integrity and contaminant free surfaces, a new bottle should be used for each test rather than attempting to clean or reuse a bottle. The bottles may be a mass-produced, machine-formed, standard-threaded, bottle that is commercially available at a cost inexpensive enough to be disposable. Such a bottle was tested and found to have a burst pressure in excess of 240 psig.

Figure 5:
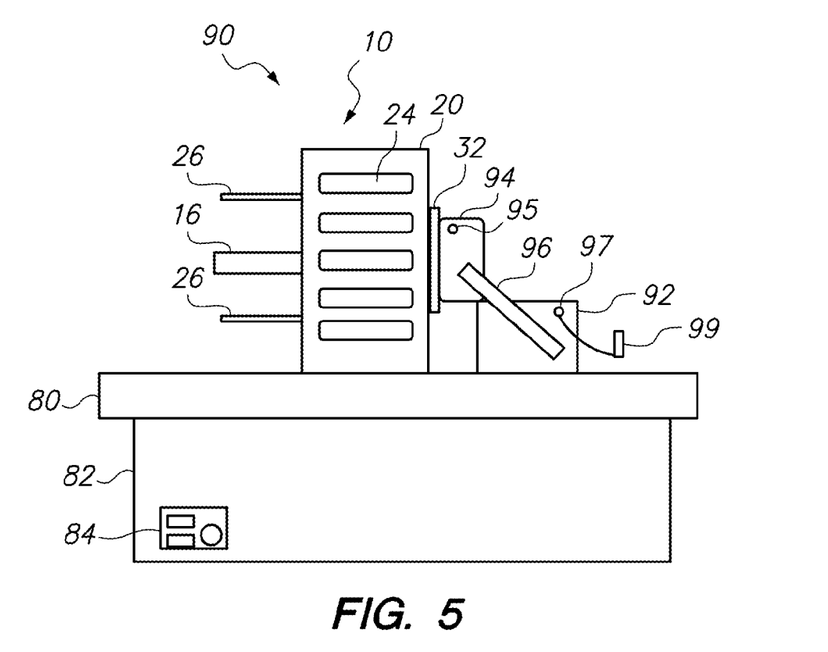
FIG. 5 is a side view of the carousel of FIG. 1 positioned sideways in shaking mode on a shaker.

FIG. 5 is a side view of a simulator 90 with the carousel 10 of FIG. 1 positioned (axially) sideways in shaking mode on a shaker table 80, including a shaker 82 with a timer and speed controller 84. The simulator may also include a fluid agitation or mixing device.

The agitation device in FIG. 5 is a reciprocal shaker 82 with a bracket 92 for mounting the carousel 10 sideways, bottles horizontal (not shown), held in by the latches (See FIG. 3) to operate in a shaking mode. Alternatively, FIG. 6 places the carousel 10 in an upright viewing mode.

A reciprocal shaker preferably does not have a wrist or elbow action arc to its throw (as say a typical paint shaker does) since that would shake the top bottles more than those on the bottom. Preferably, the shaker 82 provides a means to vary the throw length and/or frequency of the shaking so that the severity of agitation can be controlled to replicate the turbulence in the flow lines, heat exchangers, static mixers, and separation vessels. A throw distance of up to about 8 cm and a frequency up to about 4/s (240 rpm) is generally sufficient. The duration of agitation is controlled by any conventional electronic device timer, such as controller 84, suitable for precision timing of the on/off switching of an electrical appliance. The carousel 10 can remain connected to power and temperature controller 18 (See FIG. 1) while shaking, so that the temperature can be maintained indefinitely, for however long the real mixing process lasts.

Another embodiment uses one or more variable speed mixing or stiffing devices physically or magnetically coupled to a bar, blade, paddle or other mixing element inside each bottle. Mixing of the fluid may be done at a mixing station mounted at a fixed position in the stage. The bottles are mixed in sequence as the carousel is rotated past the mixer. The bottles then rotate past the observation point for images to be recorded a fixed time after they were mixed. In another embodiment, mixers are mounted under all the bottles wells and fluids are mixed while the fluids separate and images are recorded.

The simulator 90 includes a tilting mechanism that may be manually or automatically operated. As shown, the tilt mechanism includes a mounting bracket 92 and a tilting bracket 94 coupled by a structural arm 96. Pivoting of the structural arm 96 relative to the mounting bracket 92, and pivoting of the tilting bracket 94 relative to the structural arm 96 may be imparted by a pneumatic cylinder or other know motive device. The title mechanism is preferably design to secure the entire carousel to the shaker table 80 and controllably move the carousel 10 from the shaking position of FIG. 5 to the viewing position of FIG. 6. The tilting mechanism preferably also includes a hole 95 in the tilting bracket 94, a hole 97 in the mounting bracket 92, and a locking pin 99. The locking pin 99 can be inserted into the holes 95, 97 when the holes 95, 97 are aligned as in FIG. 6 in order to secure the carousel in either the vertical or horizontal position. Especially in the vertical position, the locking pin can prevent the carousel from unintentionally tipping over during the test.

Figure 6:
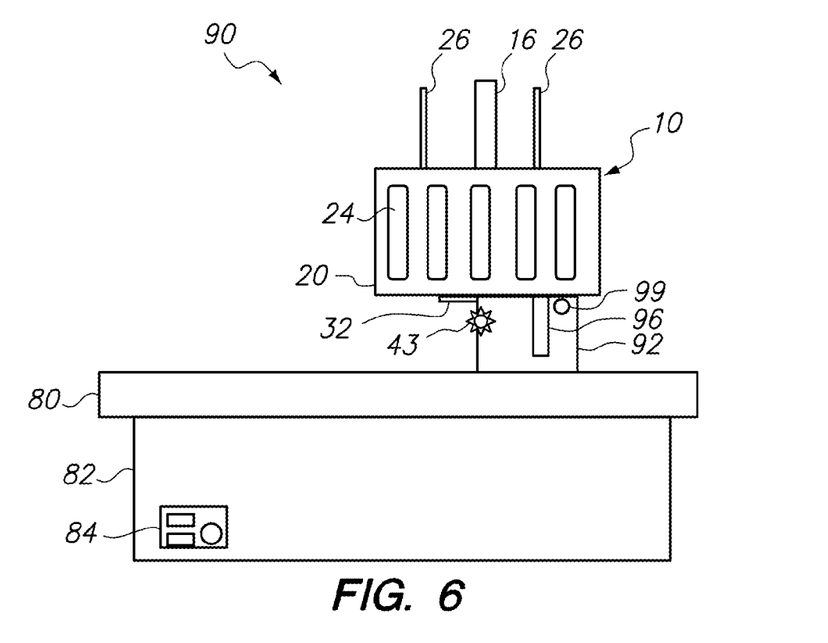
FIG. 6 is a side view of the carousel of FIG. 1 mounted upright on a shaker to rotate and view the bottles

FIG. 6 is a side view of the simulator 90 with the carousel 10 in an upright position above the shaker table. In this position, the carousel 10 may be rotated on its axis for ease of viewing the bottles, and positioning of the bottles adjacent an illumination source, such as the underside illumination source 43. In this position, each of the bottles is vertically orientated, such that the phases separate vertically with the axis of the bottles. The slits 24 allow visual observation, as well as the use of an imaging device or other types of devices for measuring the position or quality of the phases within the bottles. The holes 95, 97 are preferably positioned so that they align when the carousel 10 is in the viewing position of FIG. 6. Accordingly, the locking pin can be inserted into the holes to secure the carousel in this position.

Figure 7:
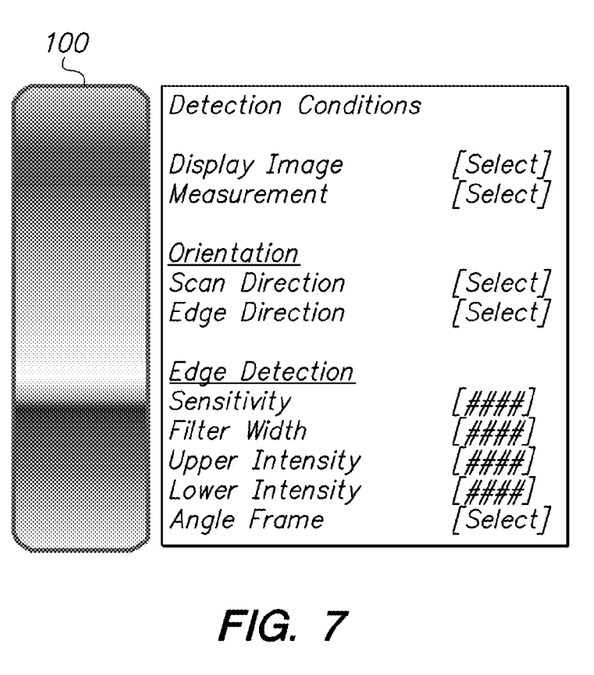
FIG. 7 is a screen shot illustrating an automated analysis of a digital image of the fluid in the bottle of FIG. 3.

FIG. 7 is a screen shot illustrating an automated analysis of a digital image 100 of the fluid in the bottle of FIG. 3. In one embodiment, an imaging device is used to record the separation of the oil and water in the test bottles. With reference to FIG. 3, the imaging device 44 may be a high resolution digital camera mounted in front of the illuminated stage with the imaging chip (e.g. charge coupled device or photomultiplier array) mapped to the vertical swatch of the bottle 60 that is visible through the slit 24. The imaging device can be operated manually or by using a controller synchronized to an automated carousel rotation to record images at desired time intervals, such that the operator need not be present during the entire time necessary to separate the emulsion. The data from the digital image is conveniently processed through an algorithm that computes the volume and the quality of the phases in the bottle, as shown in the screen shot of FIG. 7. Accordingly, photography and image analysis may be used rather than visual inspection to collect the data.

Figure 8:
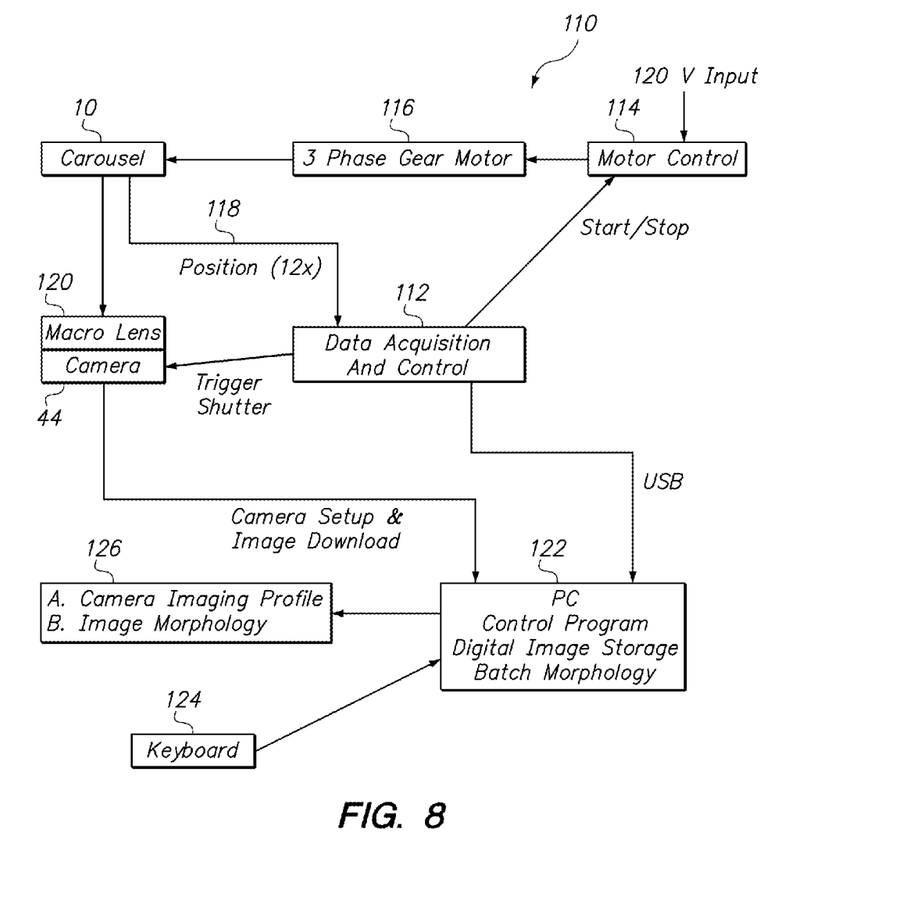
FIG. 8 is a schematic of an automated image collection system.

FIG. 8 is a schematic of an automated image collection system 110. In the embodiment shown, a data acquisition and control system 112 provides a control signal to a motor controller 114. The controller 114 then controls a three-phase gear motor 116 that rotates the carousel 10. The position of the carousel may be further detected and indicated via a signal 118 back to the control system 112. When the carousel is positioned with a selected bottle aligned with the illumination stage, the control system 112 instructs a camera 44, using a macro lens 120, to capture a digital image and send the resulting data to a computer, such as a personal computer 122. The computer 122 may receive input from a user via a keyboard 124 or other input device. The computer may further produce an output 126, including a camera imaging profile and image morphology data.

The invention is also directed to a method of using the thermal phase separation simulator to select chemical agents for thermal phase separations. In one embodiment, a fresh emulsion, as found in the thermal phase separation system to be modeled, is used, and the amount of oil and water that separate from the emulsion as a function of time is recorded to calculate the separation rate. The residual contaminants still suspended in each phase (oil and solids in water, water and solids in oil) and the volume of condensed emulsion "rag" between the two phases is also recorded and converted to a numerical scale.

A faster separation in the batch test produces a narrower condensed dispersion height in the fluid flowing through the actual separation vessel, providing more residence time to clean up the free phases and making the interface level easier to control. Residual contaminants set a limit on the ultimate quality of the free phases produced, and residual rag emulsion in the bottle will build up in the separator over time.

In performing tests with fresh emulsion from a pressurized line, the emulsion sample should be taken with enough back pressure and cooling that it is not unduly sheared or flashed into a finer emulsion (shear or shock dispersion) or coarser emulsion (shear coagulation) than exists inside the line, as this is often irreversible. If the sample has two free phases, these should be separated in the sample and then recombined into each bottle for consistency. If the sample is actively separating, it should be kept stirred while being divided into each test bottle.

The produced fluid sample should be taken from a point just before the first chemical addition that is being simulated. For each subsequent portion of the process (e.g. flow line, heat exchanger, diluent mixer, free water knockout, oil treater, or electric field coalescer) key conditions affecting the phase separation (e.g. temperature, turbulent flow regime and linear velocity, flow duration or residence time, chemical or diluent addition, free water or oil removal, electric field strength) should be recorded and emulated in the process simulator. Accordingly, the thermal phase separation simulator permits the operator to simulate these useful parameters.

A typical procedure is as follows:
1. Add sample fluids and chemical treatments to bottles.
2. Seal bottles with cap assemblies.
3. Place bottle assemblies into wells in carousel and secure with latches.
4. Plug temperature controller into main power.
5. Adjust setpoint to 120° C., and let fluid temperature equilibrate to about 100° C.
6. Verify all bottles and fittings are pressure tight (no boiling).
7. Increase setpoint to maximum planned temperature, about 20° C. above the maximum planned fluid temperature (<170° C.), and let fluid temperature equilibrate (about 60 minutes).
8. Mount carousel on shaker and shake in a manner equivalent to the agitation the fluid would receive in the process for the full length of time it would receive it. Examples:
   a. Laminar flow, 1 cm/s: Select 60 rpm, 1 cm stroke
   b. Turbulent flow, 2 cm/s: Select 120 rpm, 2 cm stroke
   c. Turbulent flow, 20 cm/s: Select 240 rpm, 8 cm stroke
9. Return the carousel to the stage and rotate through the bottles to record the fluid separation.
10. At the appropriate time add additional chemical or diluent to the bottles though the septum with a gas-tight syringe.
11. After a length of time replicating that of the first process separator, use a gas-tight syringe to transfer the appropriate fluid phase through the septum into the next separator in series. For example, after replicating the free water knockout, transfer the oil phase to another bottle to simulate the oil treater, or the water phase to another bottle to simulate the skim tank.
12. Repeat the procedure on the transferred fluid, using parameters appropriate to the next separator.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, components and/or groups, but do not preclude the presence or addition of one or more other features, integers, steps, operations, elements, components, and/or groups thereof. The terms "preferably," "preferred," "prefer," "optionally," "may," and similar terms are used to indicate that an item, condition or step being referred to is an optional (not required) feature of the invention. The corresponding structures, materials, acts, and equivalents of all means or steps plus function elements in the claims below are intended to include any structure, material, or act for performing the function in combination with other claimed elements as specifically claimed. The description of the present invention has been presented for purposes of illustration and description, but it not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A thermal phase separation simulator for testing chemicals comprising:
   a circular block heater carousel made of thermally conductive material and configured to be mounted on a support and rotated relative to the support, wherein the carousel includes a top surface, a bottom surface, an outward facing side surface, and a circular array of test wells having openings through the top surface for receiving a plurality of test bottles;
   a heating element in thermal contact with the circular block heater carousel for heating the thermally conductive material of the circular block heater carousel; and
   a thermocouple in thermal contact with the circular block heater carousel for monitoring the temperature of the thermally conductive material of the circular block heater carousel;
   each test well having an illumination port for receiving light emitted from an illumination source to illuminate the test well, and a vertical slit in the outward facing side surface of the circular block heater carousel to allow visual observation or imaging of a vertical swatch of a test bottle received in the test well.

2. The thermal phase separation simulator of claim 1, wherein each well is sized to receive a test bottle that is transparent to the illumination and able to withstand internal pressure to at least 105 psig at 170° C.

3. The thermal phase separation simulator of claim 1, further comprising:
a plurality of latches secured to the carousel, wherein each latch is positioned to selectively secure a test bottle in place within one of the wells.

4. The thermal phase separation simulator of claim 3, wherein the carousel is securely coupled to a bracket that is mounted on a shaking platform.

5. The thermal phase separation simulator of claim 4, wherein the bracket mounted on the shaking platform allows for movement of the carousel between a horizontal shaking position and an upright viewing position.

6. The thermal phase separation simulator of claim 3, further comprising:
a magnetic mixer alignable below one or more of the wells, wherein the magnetic mixer magnetically couples with a device inside the bottle to impart mixing of a fluid within the bottle.

7. The thermal phase separation simulator of claim 1, wherein the circular array of test wells are equally spaced along a circumference of the carousel.

8. The thermal phase separation simulator of claim 1, wherein the illumination source emits near infrared radiation.

9. The thermal phase separation simulator of claim 1, further comprising:
a sealable septum in a cap selectively securable to one of the bottles, wherein the septum enables the addition and removal of chemicals and process fluids using a needle and syringe.

10. The thermal phase separation simulator of claim 1, further comprising:
a compression-sealed, movable dip tube extending through a cap selectively securable to one of the bottles, wherein the dip tube enables the addition and removal of chemicals and process fluids.

11. The thermal phase separation simulator of claim 10, wherein the movable dip tube is electrically isolated and connected to a high voltage source to impose an electric field on an oil phase in a bottle that is disposed in one of the wells that is electrically grounded.

12. The thermal phase separation simulator of claim 1, further comprising:
an imaging device positioned for alignment with the vertical slit of each well in response to rotation of the carousel, wherein the imaging device captures images of a fluid in the bottles.

13. The thermal phase separation simulator of claim 12, further comprising:
a motor operatively connected to the carousel; and
a controller in electronic communication with the motor for controllably rotating the carousel.

14. The thermal phase separation simulator of claim 13, wherein the controller is configured to detect a position of the carousel.

15. The thermal phase separation simulator of claim 13, wherein the controller is in electronic communication with the imaging device for instructing the imaging device to capture an image.

16. The thermal phase separation simulator of claim 15, further comprising:
a shaking platform; and
a tilt mechanism coupled to the shaking platform, wherein the controller is in electronic communication with the tilt mechanism for controlling movement of the carousel between a horizontal shaking position and an upright viewing position, and wherein the controller is in electronic communication with shaking platform for controlling operation of the shaking platform.

17. The thermal phase separation simulator of claim 16, wherein the controller controls the throw and frequency of the shaking platform.

18. The thermal phase separation simulator of claim 1, further comprising a temperature controller in electronic communication with the heating element and configured to control the heating element to heat the carousel to at least about 100° C. for simulating process conditions for heavy crudes and bitumens.

19. The thermal phase separation simulator of claim 1, in combination with the illumination source, the illumination source illuminating each test well upon rotation of the carousel to align the illumination source with the illumination port of each test well.

\* \* \* \* \*